US012558049B2

(12) United States Patent
Hoernig

(10) Patent No.: US 12,558,049 B2
(45) Date of Patent: Feb. 24, 2026

(54) METHOD FOR GENERATING A CONTRAST-ENHANCED MAMMOGRAM RECORDING

(71) Applicant: Siemens Healthineers AG, Forchheim (DE)

(72) Inventor: Mathias Hoernig, Moehrendorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 100 days.

(21) Appl. No.: 18/478,551

(22) Filed: Sep. 29, 2023

(65) Prior Publication Data

US 2024/0108298 A1 Apr. 4, 2024

(30) Foreign Application Priority Data

Sep. 30, 2022 (DE) ..................... 10 2022 210 408.0

(51) Int. Cl.
| | |
|---|---|
| *A61B 6/50* | (2024.01) |
| *A61B 6/00* | (2024.01) |
| *A61B 6/02* | (2006.01) |
| *A61B 6/12* | (2006.01) |
| *A61B 10/00* | (2006.01) |
| *A61B 10/02* | (2006.01) |
| *G06T 5/50* | (2006.01) |
| *G06T 5/92* | (2024.01) |
| *G06T 11/60* | (2006.01) |

(52) U.S. Cl.
CPC .............. *A61B 6/502* (2013.01); *A61B 6/025* (2013.01); *A61B 10/0041* (2013.01); *A61B 10/0233* (2013.01); *G06T 5/50* (2013.01); *G06T 5/92* (2024.01); *G06T 11/60* (2013.01); *A61B 6/12* (2013.01); *A61B 6/481* (2013.01); *A61B 6/482* (2013.01); *G06T 2207/10081* (2013.01); *G06T 2207/20224* (2013.01); *G06T 2207/30068* (2013.01); *G06T 2210/41* (2013.01)

(58) Field of Classification Search
CPC ....... A61B 10/0041; A61B 6/025; A61B 6/12; A61B 6/481; A61B 6/482; A61B 6/502
See application file for complete search history.

(56) References Cited

U.S. PATENT DOCUMENTS

| | | | | |
|---|---|---|---|---|
| 2012/0134464 A1* | 5/2012 | Hoernig | ................. | A61B 6/481 378/98.12 |
| 2015/0327826 A1* | 11/2015 | Smith | .................... | A61B 10/04 600/425 |

* cited by examiner

*Primary Examiner* — Amelie R Davis
(74) *Attorney, Agent, or Firm* — Harness, Dickey & Pierce, P.L.C.

(57) ABSTRACT

A method for generating a plurality of contrast-enhanced mammograms of an examination region is described. In the method a plurality of at least two different angular positions is defined for a contrast-enhanced tomosynthesis projection recording of an examination region. At least two low-energy tomosynthesis projection recordings of the examination region are subsequently generated, starting from the at least two different angular positions, in the presence of a contrast agent. Furthermore, at least two high-energy tomosynthesis projection recordings of the examination region are generated, starting from the at least two different angular positions, in the presence of a contrast agent. Finally, at least two contrast-enhanced mammograms are generated by subtracting a respective low-energy tomosynthesis projection recording from a respective high-energy tomosynthesis projection recording for a respective angular position. In addition, a mammography system is described.

20 Claims, 3 Drawing Sheets

METHOD FOR GENERATING A CONTRAST-ENHANCED MAMMOGRAM RECORDING

CROSS-REFERENCE TO RELATED APPLICATION(S)

The present application claims priority under 35 U.S.C. § 119 to German Patent Application No. 10 2022 210 408.0, filed Sep. 30, 2022, the entire contents of which are incorporated herein by reference.

FIELD

One or more example embodiments of the present invention relates to a method for generating a plurality of contrast-enhanced mammograms. In addition, one or more example embodiments of the present invention refers to a mammography control facility. One or more example embodiments of the present invention also relates to a mammography system.

RELATED ART

Two- or three-dimensional image data, which can be used for visualizing a mapped examination object and, furthermore, also for further applications, is frequently generated with the aid of modern imaging methods.

The imaging methods are frequently based on capturing X-ray radiation. An X-ray imaging system comprises an X-ray source with which X-ray radiation is emitted in the direction of an examination object. The X-ray radiation partially penetrates the examination object and some of it is absorbed by the examination object. The transmitted portion of the X-ray radiation is detected by an X-ray detector arranged opposite the X-ray source. The X-ray source has what is known as an X-ray tube, which is operated with a predetermined X-ray voltage.

One particular type of X-ray system is a mammography system, which is embodied specifically for imaging the breast of a person. Apart from imaging the breast, in many cases a biopsy of breast tissue has to be carried out in order to clarify a conspicuous finding.

What is known as a needle biopsy with X-ray imaging is used as an interventional method for this in order to take samples from the breast for a histological examination. Before carrying out the needle biopsy, a region or a structure, which justifies the removal of tissue, is typically identified on the basis of a screening.

In the case of stereo biopsy, typically two 2D X-ray recordings are created at known angles (for example –15°, +15°) ("2D" is an abbreviation for "two-dimensional"). Depth information and the positioning of the needle for the needle biopsy can be determined from this pair of images.

In addition, tomosynthesis biopsy is also used in which what is known as scouting takes place via 2D stereo imaging or 3D tomosynthesis imaging ("3D" is an abbreviation for "three-dimensional"). The final targeting of the needle can then likewise take place with the aid of 2D stereo imaging or 3D tomosynthesis imaging.

The problem with current solutions consists in that some lesions cannot be identified, or can only be identified with difficulty, in the X-ray image. Additional items of information apart from the morphology of the breast—such as items of functional information, such as the accumulation of iodine contrast agent in the region of lesions with a large number of supplying blood vessels, have not previously been included in angiogenesis—in the biopsy method and its supporting imaging. Morphological information should be taken to mean data, which characterizes the structure and form of an examination region. Functional or items of physiological information refer to functional connections, in particular relating to biophysical vital processes in the cells, tissues and organs of an animate being.

A further problem consists in the duration of a single tomosynthesis recording, because the duration is approximately between seven and 30 seconds. Since in the case of a CEDET recording (CEDET is an acronym for "Contrast Enhanced Dual Energy Tomosynthesis") two such recordings are required, a total of between 15 and 60 seconds is required for such a recording plus time for a filter change.

Methods of image-assisted breast biopsy are stereo biopsy and tomosynthesis-assisted biopsy. There are also MRT and ultrasound-assisted biopsies and vacuum biopsy methods.

Biopsy scout imaging and targeting imaging can take place via contrast agent-enhanced tomosynthesis from two timely, recombined tomosynthesis representations and a subsequent weighted subtraction of the volumes. However, generating two complete recombined tomosynthesis representations is time-consuming and is thereby also associated with increased exposure of a patient to radiation. An image recording of an examination region for ascertaining a biopsy position a biopsy needle should be conceived of as targeting imaging.

SUMMARY

Example embodiments provide a mammography method and an apparatus, in particular for ascertaining a position of a biopsy needle, which make possible a shorter recording duration and lower exposure of a patient to radiation with a capacity to identify lesions that is comparable to the prior art.

This is achieved by a method for generating a plurality of contrast-enhanced mammograms of an examination region as claimed in claim 1, by a mammography control facility as claimed in claim 12 and by a mammography system as claimed in claim 13.

BRIEF DESCRIPTION OF THE DRAWINGS

The invention will be explained in more detail below with reference to the accompanying figures and on the basis of exemplary embodiments. In the drawings.

DETAILED DESCRIPTION

Figure 1:
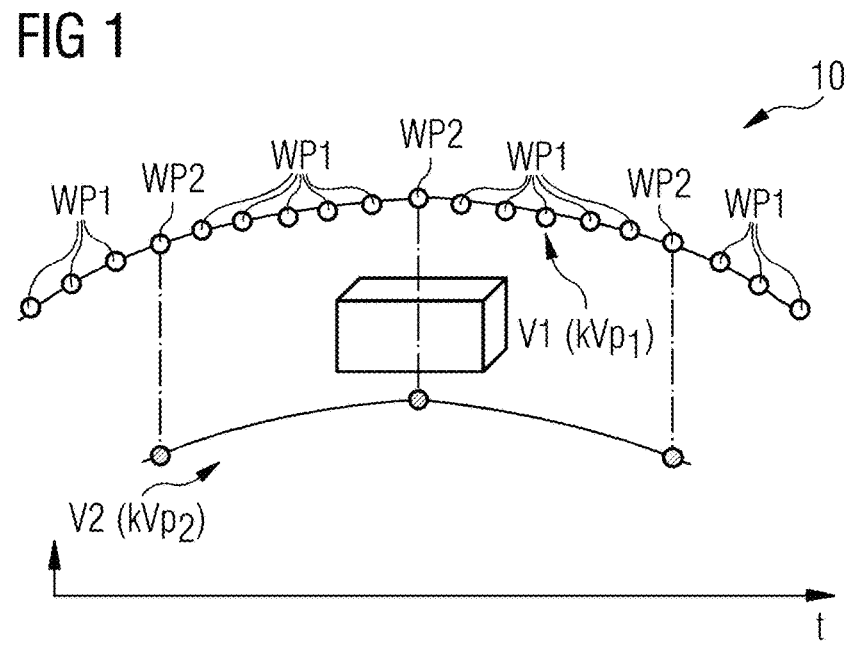
FIG. 1 shows a schematic representation of generation of a plurality of mammograms according to one exemplary embodiment of the invention.

In the inventive method for generating a plurality of contrast-enhanced mammograms of an examination region, preferably in a breast biopsy procedure, firstly a plurality of different angular positions is defined for a contrast-enhanced tomosynthesis projection recording. Advantageously, the different angular positions can be defined as a function of prior items of information about the position of a lesion. The radiologist is not tied to a rigid 15° stereo image pair and instead can also select other angular positions for the acquisition of projection recordings of the breast.

At least two low-energy tomosynthesis projection recordings of the examination region are then generated, starting from the at least two different angular positions, in the presence of a contrast agent. In this connection, a "recording" should be taken to mean an acquisition of measurement data of an examination region, in particular of the breast of a male or female patient for generating image data, but also the image data should itself be taken to mean a "recording". A "contrast-enhanced recording" should be taken to mean that the respective recording takes place in the presence of contrast agent in the examination region. The angular positions are selected such that the examination region is pictorially captured from different directions in order to generate stereo image data, preferably 3D image data, of the examination region.

Furthermore, at least two high-energy tomosynthesis projection recordings of the examination region are additionally generated, starting from the at least two angular positions, in the presence of a contrast agent. A "high-energy" tomosynthesis projection recording should be taken to mean a tomosynthesis projection recording with an X-ray energy above an energy value of an X-ray edge of the contrast agent used for the contrast imaging. As will be explained later, a plurality of "high-energy" tomosynthesis projection recordings can also be generated with different energies: a "mid energy" and a "high-energy", with both types of energy preferably lying above the energy of the X-ray edge of the contrast agent, preferably iodine, used for contrast imaging.

Finally, at least two contrast-enhanced mammograms are generated by subtracting the low-energy tomosynthesis projection recording from the high-energy tomosynthesis projection recording for a respective angular position.

A contrast-enhanced mammogram should be taken to mean a 2D image representation of the human breast, preferably of the female breast, assisted by a contrast agent, preferably iodine, with regard to the image contrasts.

Items of 3D information or stereo information are obtained of the examination region on the basis of the combination of the items of information of the contrast-enhanced mammograms, which were recorded from different angles. Firstly, contrast-enhanced 2D items of image information are therefore obtained from the different angular positions of the respective tomosynthesis projection recordings, which optionally correspond in terms of perspective to a conventional mammogram recording in which, however, physiological or functional information in respect of the mapped breast is also represented owing to the administration of contrast agent.

As will be explained in detail below, it is particularly advantageous that items of stereo information or even 3D representations can be obtained by way of a recombination of the mammograms initially present as projections, as well as from a recombination of the tomosynthesis projection recordings. In particular, what are known as recombined native or contrast-enhanced recombined tomosynthesis representations can be obtained.

A recombined tomosynthesis representation is ascertained on the basis of a plurality of individual recordings, also referred to as projections or tomosynthesis projection recordings, which are generated from a plurality of different angular positions and are used to obtain items of stereo information about an examination region. The image data generated on the basis of these projections from different angular directions is combined to form a 3D image in order to obtain items of information about the depth position of a section of interest, in particular of a lesion.

At least two contrast-enhanced mammograms are obtained with the inventive method, which, combined, supply certain items of depth information with regard to the position of a lesion in the examination region. Additional items of physiological information can be obtained by way of the information about iodine-accumulating regions. The inventive method can be used in the context of a biopsy for the recording of a scout image as well as in the contest of targeting. "Targeting" should be taken to mean ascertaining a 3D position of a section of the breast of a female patient to be actuated by a biopsy. A scout image provides an overview of an examination region and facilitates planning and, in particular, parameterization of a mammography examination.

Furthermore, the biopsy samples that have been taken can also be imaged in order to ascertain whether the contrast agent has accumulated in the images of the samples. A direct correlation between the sample and the position in the breast can be established thereby. The samples taken can thus be checked quickly and directly, preferably by way of a spectral CEDEM pair of recordings (CEDEM is an acronym for "Contrast-enhanced Dual-Energy Mammography").

The inventive mammography control facility has a defining unit for defining a plurality of at least two different angular positions for a contrast-enhanced tomosynthesis projection recording of an examination region of a breast of a male patient or a female patient.

The inventive mammography control facility also includes an actuation unit for generating at least two low-energy tomosynthesis projection recordings of an examination region, starting from the plurality of different angular positions, and for generating at least two high-energy tomosynthesis projection recordings of the examination region, starting from the at least two angular positions, in the presence of a contrast agent.

The inventive mammography control facility also has a subtraction unit for generating at least two contrast-enhanced mammograms by subtracting the low-energy tomosynthesis projection recording from the high-energy tomosynthesis projection recording for a respective angular position. The inventive mammography control facility shares the advantages of the inventive method for generating at least two contrast-enhanced mammograms.

The inventive mammography system has an X-ray source for emitting X-ray radiation, an X-ray detector unit for detecting the emitted X-ray radiation and the inventive mammography control facility for actuating the X-ray source and for evaluating the X-ray radiation detected by the X-ray detector unit.

The inventive mammography system shares the advantages of the inventive method for generating at least two contrast-enhanced mammograms.

The inventive computer program product has program code segments with which all steps of the inventive method are carried out when the program is executed in the mammography system.

An implementation largely in terms of software has the advantage that existing mammography systems or their control facilities can be easily retrofitted by way of a software update in order to work in the inventive manner.

A majority of the above-mentioned components of the inventive mammography control facility can be implemented completely or partially in the form of software modules in a processor of a corresponding computing system, for example of a control facility of a mammography system or a computer, which is used for controlling such a system. An implementation largely in terms of software has the advantage that even previously used computing systems can be easily retrofitted by way of a software update in order to work in the inventive manner. In this respect the object is also achieved by a corresponding computer program product with a computer program, which can be loaded directly into a computing system, with program segments in order to carry out the steps of the inventive method for generating at least two contrast-enhanced mammograms, in particular the steps for defining a plurality of at least two different angular positions for a contrast-enhanced low-energy tomosynthesis projection recording, for generating at least two low-energy tomosynthesis projection recordings, for generating at least two high-energy tomosynthesis projection recordings and for generating at least two contrast-enhanced mammograms by subtracting the contrast-enhanced low-energy tomosynthesis projection recording from the high-energy tomosynthesis projection recording for a respective angular position, when the program is executed in the computing system. Apart from the computer program, a computer program product of this kind can optionally comprise additional component parts, such as documentation and/or additional components, also hardware components, such as hardware keys (dongles, etc.), in order to use the software.

A computer-readable medium, for example a memory stick, a hard drive or another transportable or permanently installed data carrier, can serve for transport to the computing system or to the control facility and/or for storage on or in the computing system or the control facility, on which medium the program segments of the computer program, which can be read and executed by a computing system, are stored. The computing system can have, for example, one or more cooperating microprocessor(s) or the like for this.

The dependent claims and the following description contain particularly advantageous embodiments and developments of the invention respectively. In particular, the claims of one category of claims can also be developed analogously to the dependent claims of another category of claims. In addition, the various features of different exemplary embodiments and claims can also be combined as part of the invention to form new exemplary embodiments.

In a preferred embodiment of the inventive method for generating a plurality of contrast-enhanced mammograms of an examination region, the plurality of at least two different angular positions comprises at least three different angular positions.

Furthermore, the plurality of different angular positions is divided in this embodiment into first angular positions and second angular positions, with the second angular positions comprising at least two different angular positions. At least two different angular positions are required in order to obtain items of depth information of a position of a region to be mapped, in particular of a possible lesion.

The low-energy tomosynthesis projection recording is generated starting from the first angular positions and the second angular positions. The high-energy tomosynthesis projection recordings are generated starting from the second angular positions.

In addition to the contrast-enhanced mammograms, a recombined tomosynthesis representation is generated in this embodiment on the basis of the low-energy tomosynthesis projection recordings, starting from the first angular positions and second angular positions.

thesis projection recordings, starting from the first angular positions and second angular positions.

The idea behind the division of the angular positions into first and second angular positions consists in reducing the number of contrast-enhanced high-energy tomosynthesis projection recordings, which are required for generating the contrast-enhanced mammograms of the examination region, to an optimally low number, which is still sufficient for obtaining certain items of depth information in the examination region.

The second angular positions are complementary to the first angular positions. The first and second angular positions each form non-overlapping, genuine subsets of the plurality of different angular positions. As the number of second angular positions for the contrast-enhanced high-energy tomosynthesis projection recordings is reduced compared to the number angular positions, which are actuated in the case of the low-energy tomosynthesis projection recordings, the overall time for generating the contrast-enhanced mammograms and the recombined 3D tomosynthesis representation can be reduced with respect to two complete sets of tomosynthesis projection recordings and the radiation dose to which a patient is subjected is also reduced therewith. With the recombined tomosynthesis representation on the basis of the low-energy tomosynthesis projection recordings, a three-dimensional representation of the examination region is possible at least approximately if an adequate number of low-energy tomosynthesis projection recordings is generated. A recombined tomosynthesis representation should be taken to mean what is known as a tomosynthesis volume, i.e. a 3D representation of the examination region, for the generation of which, items of image information from projections from the first and second angular positions are used. Advantageously, the user receives morphological 3D items of information of enhanced quality in addition to the items of physiological information obtained on the basis of the at least two contrast-enhanced mammograms. Advantageously, it is possible to switch between images with morphology information and physiology information if these are represented either side by side or superimposed on each other. Owing to the time saving compared to two complete tomosynthesis recordings, the time during which the breast has to compressed can also be reduced, whereby the patient's comfort level is improved or a possible health burden due to the compression of the breast is reduced.

Preferably, a first current-time product for actuating an X-ray source for generating the low-energy tomosynthesis projection recordings is used in the inventive method for generating a plurality of contrast-enhanced mammograms in the step of generating the low-energy tomosynthesis projection recordings of an examination region at the first angular positions. A second current-time product is used for actuating the X-ray source for generating the low-energy tomosynthesis projection recordings at the second angular positions. The second current-time product for actuating the X-ray source for generating the contrast-enhanced high-energy tomosynthesis projection recordings is used in the step of generating high-energy tomosynthesis projection recordings of the examination region.

Advantageously, the first current-time product can be selected such that its value is adjusted to requirements of a native tomosynthesis projection recording with which, primarily, items of morphological information of the examination region are to be obtained. The projections, which are obtained from the first angular positions, are primarily used for obtaining stereo data of the examination region. The first current-time product tends to be selected so as to be low in order to keep the dose uptake of the patient as low as possible. By contrast, the second current-time product for obtaining projections for a contrast-enhanced image representation or contrast-enhanced mammograms of the examination region is selected to be higher compared to the first current-time product in order to keep the contrast and the image quality as high as possible for the contrast-enhanced mammograms. The contrast-enhanced mammograms are primarily used to obtain items of physiological information of the examination region. The items of physiological information can be obtained as stereo data on the basis of a recombined tomosynthesis representation, which is generated on the basis of tomosynthesis projection recordings, which were recorded starting from the second angular positions. However, individual mammograms can also be used for obtaining items of physiological information, which are generated on the basis of the individual projections or tomosynthesis projection recordings, which were recorded from the second angular positions.

Particularly preferably, the value of the second current-time product is set higher than the value of the first current-time product. Those projections, which are obtained for a subtraction for generating contrast-enhanced mammograms, are therefore acquired with a higher current-time product. Advantageously, the quality of the contrast-enhanced mammograms or a contrast-enhanced, recombined tomosynthesis representation resulting from them is improved.

In a preferred variant of the inventive method for generating a contrast-enhanced mammogram, the second angular positions comprise the angular positions $-15°$, and $15°$. The two said angular positions are typically used for a stereo biopsy with 2D X-ray recordings from two different angles. An item of depth information and the positioning of the needle for the biopsy can be ascertained from such a pair of images. Advantageously, a known $15°$ stereo procedure can be easily recreated for the radiologist.

The second angular positions likewise preferably comprise the angular position $0°$. Advantageously, the high-energy tomosynthesis projection recordings also comprise a frontal recording of the examination region. The projection from the angular position $0°$ can be advantageously used for generating a pair of scout images. A pair of scout images of this kind has a non-contrast, synthetic mammogram and a contrast-enhanced image recording from the frontal angular position $0°$. Advantageously, items of physiological information can also be used for the localization of sections of the examination region, which are relevant to a biopsy.

The first angular positions preferably also comprises at least three angular positions, preferably at least seven, most preferably between nine and 25 angular positions. More exact items of 3D image information can be obtained, the greater the number of projections is selected to be for generating the low-energy tomosynthesis projection recordings. In particular, the more projections from different angular positions contribute to a recombined low-energy tomosynthesis representation, the more the image artifacts are reduced. Preferably, said projections also always comprise a projection from the angular position $0°$, so a frontal plan view of the examination region is preferably obtained.

In one embodiment of the inventive method for generating a plurality of contrast-enhanced mammograms of an examination region, the second angular positions comprise one of the following projections:

CC,

MLO.

"CC" stands for "cranio-caudal", i.e. a projection from the $0°$ angular position, clearly expressed by "top".

"MLO" stands for "medio-lateral-oblique", clearly expressed for a projection "from the side". Advantageously, it is possible to detect lesions which are hidden by fatty tissue in some directions more easily by way of these different views. Advantageously, these typical perspectives are made available to the user as part of the inventive method.

In a particularly preferred variant of the inventive method for generating a plurality of contrast-enhanced mammograms of an examination region, the second angular positions are defined as a function of the angular positions of previous recordings. Advantageously, the second angular positions can be selected such that the suspected lesions are struck by the central beam of the X-ray projection or are located very close to the path of the central beam of the X-ray projection if it may be identified on the basis of the previous recordings. Advantageously, the image quality of the individual contrast-enhanced mammograms and of a contrast-enhanced recombined tomosynthesis representation is thus improved by selecting suitable angular positions.

The second angular positions are likewise preferably defined as a function of the z-position of a suspected lesion. Advantageously, the second angular positions can be selected as a function of the z-position of a suspected lesion such that the suspected lesion is struck by the central beam of the X-ray projection or is located very close to the path of the central beam of the X-ray projection. Advantageously, the image quality of the contrast-enhanced mammograms and of a contrast-enhanced recombined tomosynthesis representation resulting therefrom is thus improved by selecting suitable angular positions of the individual tomosynthesis projection recordings. The z-direction corresponds to an irradiation direction from the $0°$ direction; it is oriented in the "thickness direction" or "height direction" of the examined object.

In a preferred variant of the inventive method for generating a plurality of contrast-enhanced mammograms of an examination region, the spectral tomosynthesis projection recordings are corrected for scattered radiation before the subtraction. Advantageously, the image quality of the contrast-enhanced tomosynthesis projection recordings is further improved by the correction of the scattered radiation.

In one variant of the inventive method, a further energy is incorporated in the (spectral) scan (the scans, "scan" is used synonymously with "recording" here), in particular for determining thickness maps for the iodine representation or calculation of image representations with more than two different types of contrast or material or tissue. Preferably, examination regions with fatty tissue, glandular tissue and with contrast agent or with muscle tissue, fatty tissue and with contrast agent are reproduced. Preferably, an X-ray radiation energy of 28 kVp with a low-energy filter, which preferably comprises rhodium or aluminum as the filter material, is used as the low energy for the case of the use of iodine as the contrast agent and an X-ray radiation energy of 34 kVp, which lies slightly above the iodine absorption edge of 33 kVp, with a high-energy X-ray filter or mid-energy X-ray filter, which preferably comprises titanium, is used as the mid energy and an X-ray radiation energy of 49 kVp with a high-energy X-ray filter, which preferably comprises copper or titanium, is used as the high energy. Advantageously, an improved separation of material can be achieved in the pictorial representation of an examination region.

In one embodiment of the inventive method for generating a plurality of contrast-enhanced mammograms, one of the following images is ascertained on the basis of the generated tomosynthesis projection recordings and mammograms and preferably provided for a breast biopsy for generating a scout recording or a targeting recording for a contrast agent-enhanced image representation:

a digital recombined low-energy breast tomosynthesis representation for a reproduction of the 3D morphology of a breast to be biopsied, a contrast-enhanced recombined tomosynthesis representation for functional or physiological 3D imaging, with, for example or preferably, the contrast agent accumulation in an examination region being pictorially represented, a synthetic low-energy 2D mammogram, also referred to as a synthetic mammogram, which can preferably be used as an overview recording, in particular as a scout recording, a synthetic contrast-enhanced mammogram for functional imaging, preferably as an overview recording, particularly preferably as a scout-recording, a low-energy mammogram for a first angular position from a tomosynthesis projection recording, preferably for representing the morphology, preferably for stereotactic targeting, a low-energy mammogram for a second angular position from a tomosynthesis projection recording, preferably for representing the morphology, for example for stereotactic targeting, a mammogram processed from a tomosynthesis projection recording for a second angular position, a contrast-enhanced mammogram for a second angular position for functional imaging, as is preferably implemented by a representation of a contrast agent accumulation in lesions and blood vessels in the breast, which supply the lesions with blood, a mammogram based on a low-energy tomosynthesis projection recording overlaid with a contrast-enhanced recombined tomosynthesis representation, a targeting recording, which comprises overlaying a low-energy tomosynthesis projection recording and a recombined low-energy tomosynthesis representation, and/or a contrast-enhanced recombined tomosynthesis representation, a projection image of a low-energy tomosynthesis projection recording overlaid with an image representation of a contrast-enhanced mammogram.

Advantageously, a large number of different image representations can be obtained for different purposes on the basis of the projections obtained with at least two different spectra.

A digital recombined low-energy breast tomosynthesis representation is used particularly advantageously for obtaining morphological stereo data of the breast. A "representation" should in this case be taken to mean a pictorial 3D representation of a plurality of corresponding low-energy breast tomosynthesis projection recordings. A recombined low-energy breast tomosynthesis representation of this kind is based on a plurality of low-energy breast tomosynthesis projection recordings from first and second angular positions.

A contrast-enhanced recombined tomosynthesis representation is preferably used for ascertaining physiological stereo data or 3D data (for example by way of a weighted subtraction of the high-energy breast tomosynthesis projection recordings from the corresponding low-energy breast tomosynthesis projection recordings) of the breast.

Individual contrast-enhanced mammograms from individual angular positions can be used for ascertaining items of physiological information from particular directions.

If a mammogram is overlaid with a contrast-enhanced recombined tomosynthesis representation, it is possible to localize individual relevant regions more exactly and/or more quickly.

For the task of targeting, conventional non-contrast, recombined tomosynthesis representations or stereo recordings can be used for obtaining items of morphological information on the basis of the captured projections and, parallel therewith, the contrast-enhanced recombined tomosynthesis representation can be used for obtaining items of physiological information.

In one variant of the inventive method for generating a plurality of contrast-enhanced mammograms, targeting takes place, that is to say, determining the x,y,z-coordinates of the lesion to be biopsied, in one of the following image representations:

in the contrast-enhanced mammograms on the basis of the tomosynthesis projection recordings of the second angular positions, in the contrast-enhanced mammograms on the basis of the tomosynthesis projection recordings of the second angular positions and/or in the low-energy tomosynthesis projection recordings of the second angular positions, in the contrast-enhanced mammograms on the basis of the tomosynthesis projection recordings of the second angular positions and/or in the recombined low-energy tomosynthesis representations of the second angular positions and/or first angular positions.

Apart from the generated contrast-enhanced mammograms, items of additional information can be obtained for the targeting from individual low-energy tomosynthesis projection recordings or also from 3D tomosynthesis representations. The recordings from the direction of the first and/or the second angular positions can be used in this case.

FIG. 1 shows a schematic representation 10 of generation of a plurality of mammograms according to one exemplary embodiment of the invention.

An upper section of the schematic representation 10 represents a plurality of first angular positions WP1 and second angular positions WP2 (only 16 first angular positions WP1 are represented, but a total of 22 first angular positions WP1 is preferred, which with three second angular positions WP2 preferably comprise a total angular range of 50°), which are adopted by an X-ray source of a mammography system in the case of a low-energy tomosynthesis recording for obtaining a total of 25 low-energy tomosynthesis projection recordings CET-LE. Preferably, the values −15°, 0°, +15° are selected for the three second angular positions WP2.

The second angular positions WP2 are adopted by an X-ray source of a mammography system in the case of a low-energy tomosynthesis projection recording CET-LE as well as in the case of a high-energy tomosynthesis projection recording CET-HE for obtaining a total of 6 projections. The current-time product of the X-ray source is preferably increased in the case of the three second angular positions WP2, because the low-energy tomosynthesis projection recordings CET-LE associated with the second angular positions WP2 are also required for generating a contrast-enhanced mammogram KMA and an increased current-time product reduces noise effects in the case of increased absorption, as occurs with contrast-enhanced imaging.

The 22 projections for the low-energy tomosynthesis projection recordings CET-LE, starting from the first angular positions WP1, are preferably generated with a lower first X-ray voltage V1 of the X-ray tube of the X-ray source of the mammography system. The three low-energy tomosynthesis projection recordings CET-LE, starting from the second angular positions WP2, are also preferably generated with a lower first X-ray voltage V1 of the X-ray tube of the X-ray source of the mammography system. Three high-energy tomosynthesis projection recordings CET-HE are subsequently generated at the second angular positions WP2 with a second X-ray voltage V2 (kVp2), which is higher than the first X-ray voltage. In a further embodiment, the sequence of the acquisitions can be swapped.

"Subsequently" can mean that in the case of the second angular positions there is a changeover directly following the low-energy recording with the lower first X-ray voltage V1 (kVp1) to the higher X-ray voltage V2 (kVp2) respectively and the high-energy recording takes place at the same angular position and there is subsequently a changeover back to the lower X-ray voltage V1 (kVp1) and the process continues with the carrying out of low-energy recordings, etc. FIG. 1 indicates a procedure of this kind with the timeline t at which the high-energy recordings take place at a particular second solid angle position WP2 approximately at the same time as the low-energy recordings at the same solid angle position WP2.

Alternatively, the 25 low-energy tomosynthesis projection recordings CET-LE can also be acquired first and subsequently at least the three high-energy tomosynthesis projection recordings CET-HE are obtained in the return flow, with the X-ray source being controlled in the opposite direction to the direction of the low-energy tomosynthesis projection recordings.

Contrast-enhanced mammograms KMA are finally obtained by subtraction of the low-energy tomosynthesis projection recordings CET-LE and the high-energy tomosynthesis projection recordings CET-HE having the same angles.

A contrast-enhanced recombined tomosynthesis representation (such as slices, volumes) or 3D mammogram recording is finally obtained by subtracting all low-energy tomosynthesis projection recordings CET-LE and the high-energy tomosynthesis projection recordings CET-HE having the same angles, with subsequent back projection or by way of a weighted subtraction of a recombined low-energy tomosynthesis representation from a recombined high-energy tomosynthesis representation.

Figure 2:
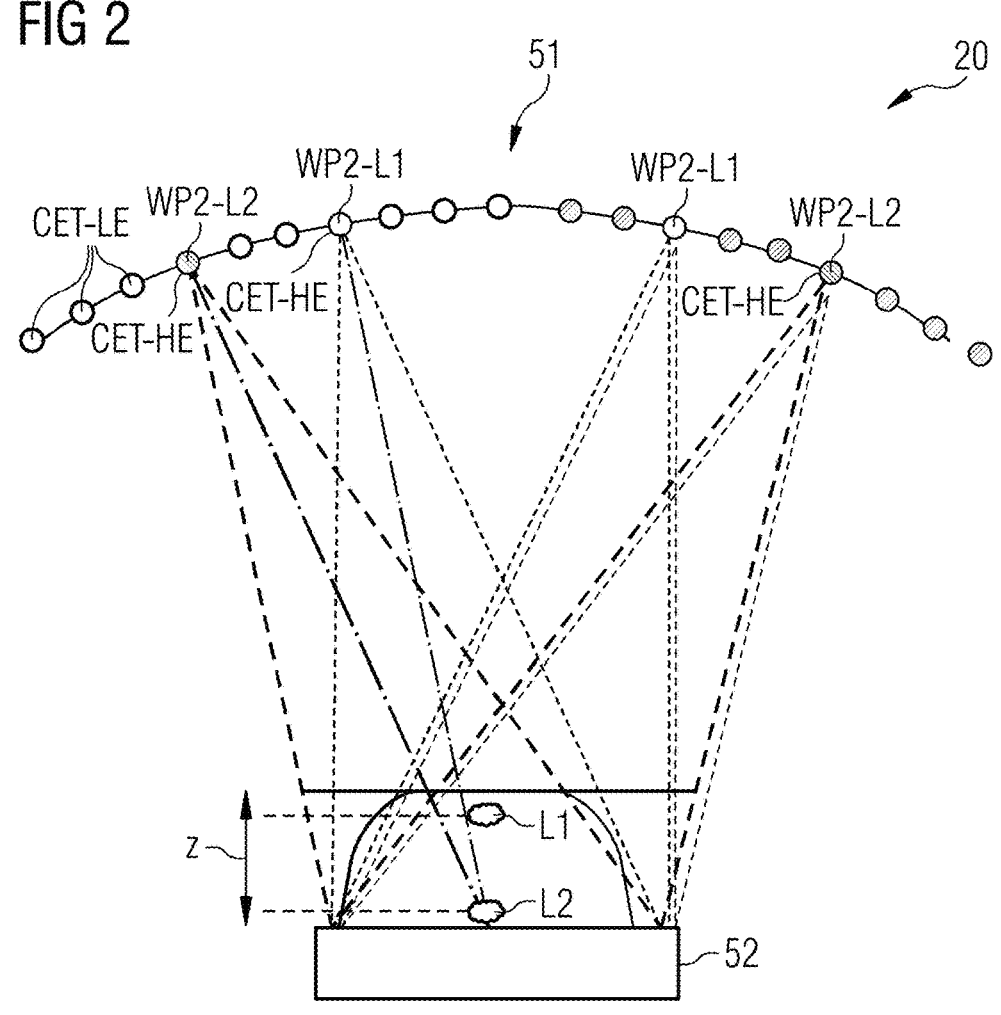
FIG. 2 shows a schematic representation of the selection of different position angles as a function of a different depth position of a suspected lesion.

FIG. 2 illustrates a schematic representation 20 of the selection of different second angular positions WP2 for generating a contrast-enhanced mammogram KMA as a function of a different depth position z of a suspected lesion L1, L2. If the lesion L1 is located at a greater height above the X-ray detector 52, i.e. in FIG. 2 further above the X-ray detector 52, further removed from the X-ray detector 52, the high-energy tomosynthesis projection recordings CET-HE at a second angular position WP2-L1 are carried out at a relatively small angle of the X-ray source 51. Advantageously, the lesion L1 is thus located more in the center of the central beam. If the lesion L2 is located at a lower height above the X-ray detector 52, i.e. in FIG. 2 closer to the X-ray detector 52, the high-energy tomosynthesis projection recordings CET-HE at a second angular position WP2-L2 of the X-ray source 51 are carried out at a greater angle and improved control information is obtained compared to selection of a small angle.

Figure 3:
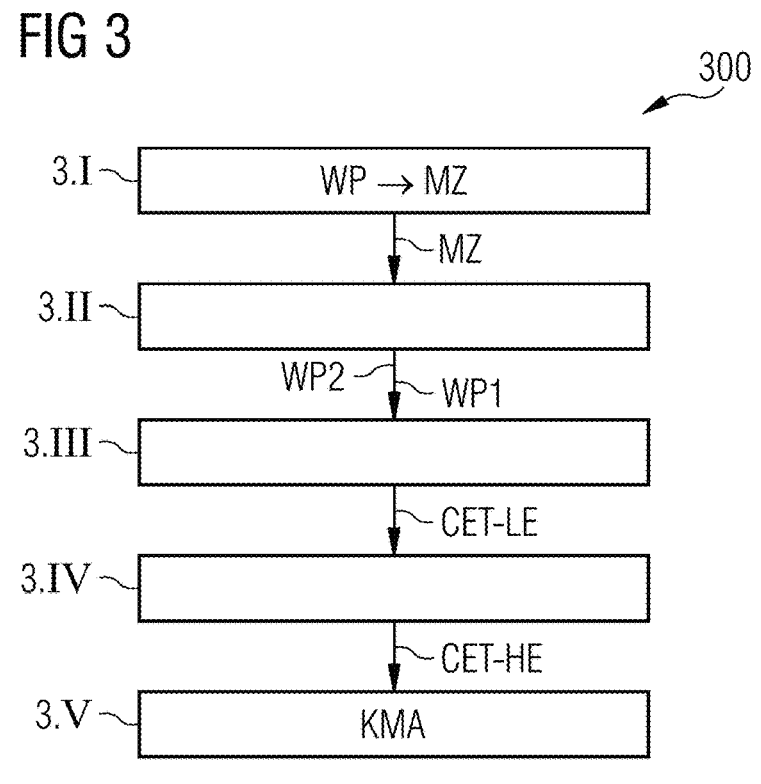
FIG. 3 shows a flowchart, which illustrates a method for generating a plurality of contrast-enhanced mammograms according to one exemplary embodiment of the invention, FIG. 4 show a schematic representation of a mammography control facility according to one exemplary embodiment of the invention.

FIG. 3 shows a flowchart 300, which illustrates a method for generating a plurality of contrast-enhanced mammograms according to one exemplary embodiment of the invention.

In step 3.I, a plurality MZ of different angular positions is defined for a plurality of low-energy tomosynthesis projection recordings of an examination region. Defining the different angular positions WP can be ascertained, for example, on the basis of a previous recording and an estimated depth position or z-position of a lesion or a relevant examination region.

In step 3.II, the plurality MZ of different angular positions WP is divided into first angular positions WP1 and second angular positions WP2, wherein the second angular positions WP2 are to be used for obtaining a plurality of contrast-enhanced mammograms KMA whose combination supplies items of stereo information. The second angular positions WP2 can be selected as a function of an estimated depth position or z-position of a lesion or a relevant examination region, as has already been explained in connection with FIG. 2.

In step 3.III, a plurality of low-energy tomosynthesis projection recordings CET-LE of an examination region is generated starting from the plurality MZ of different angular positions WP. That is to say, the different angular positions WP are actuated by the X-ray source of a mammography system and a projection with a low X-ray voltage of an X-ray tube of a mammography system is recorded from each of the angular positions WP.

In step 3.IV, a plurality of high-energy tomosynthesis projection recordings CET-HE of the examination region are generated starting from the second angular positions WP2 generated.

Finally in step 3.V, a plurality of contrast-enhanced mammograms KMA is generated by subtracting the contrast-enhanced low-energy tomosynthesis projection recordings CET-LE from the high-energy tomosynthesis projection recordings CET-HE for the second angular positions WP2.

Figure 4:
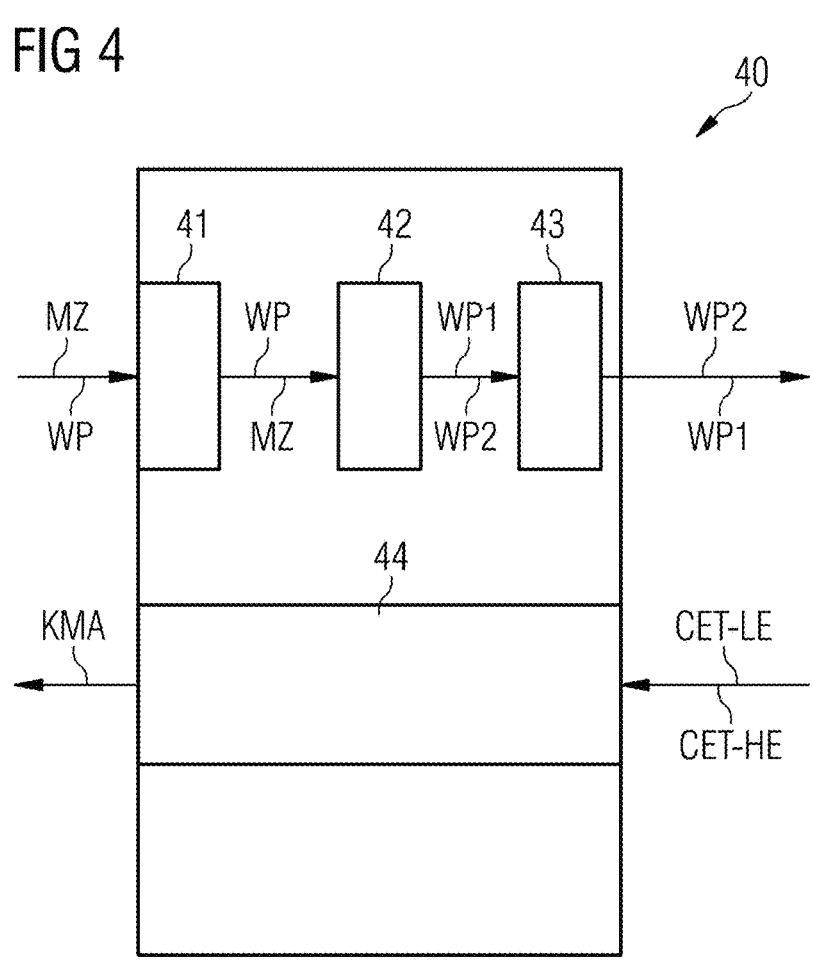

FIG. 4 illustrates a schematic representation of a mammography control facility 40 according to one exemplary embodiment of the invention.

The mammography control facility 40 has a defining unit 41 for defining a plurality MZ of different angular positions WP.

In addition, the mammography control facility 40 comprises a dividing unit 42 for dividing the plurality MZ of different angular positions WP into first angular positions WP1 and second angular positions WP2.

The mammography control facility 40 also includes an actuation unit 43 for generating a plurality of low-energy tomosynthesis projection recordings CET-LE of an examination region, starting from the plurality MZ of different angular positions WP, and for generating a plurality of high-energy tomosynthesis projection recordings CET-HE of the examination region, starting from the second angular positions WP2.

The mammography control facility 40 also has a subtraction unit 44 for generating a plurality of contrast-enhanced mammography recordings KMA by subtracting the low-energy tomosynthesis projection recordings CET-LE from the high-energy tomosynthesis projection recordings CET-HE for the second angular positions WP2. The subtraction unit 44 is also configured to generate or output additional image representations, in particular low-energy tomosynthesis projection recordings CET-LE and high-energy tomosynthesis projection recordings CET-HE as well as recombined tomosynthesis projection representations, which are obtained on the basis of the low-energy tomosynthesis projection recordings CET-LE or the high-energy tomosynthesis projection recordings CET-HE by recombination.

Figure 5:
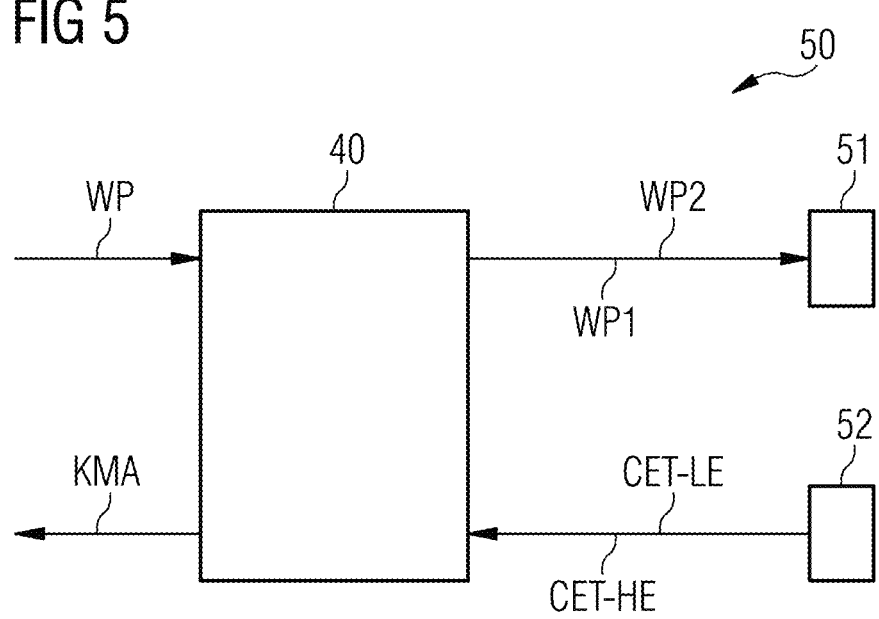
FIG. 5 shows a schematic representation of a mammography system according to one exemplary embodiment of the invention.

FIG. 5 shows a schematic representation of a mammography system 50 according to one exemplary embodiment of the invention.

The mammography system 50 comprises an X-ray source 51 for emitting X-ray radiation, an X-ray detector unit 52 for detecting the emitted X-ray radiation, and the mammography control facility 40 illustrated in FIG. 4. The generated low-energy tomosynthesis projection recordings CET-LE and high-energy tomosynthesis projection recordings CET-HE detected by X-ray detector unit 52 are evaluated by the mammography control facility 40 and the mammography control facility 40 generates a plurality of contrast-enhanced mammography recordings KMA, which, recombined with each other, supply items of stereo information.

To conclude, reference is made once again to the fact that the above-described detailed methods and structures are exemplary embodiments and that the basic principle can also be varied within wide ranges by a person skilled in the art without departing from the field of the invention insofar as it is predefined by the claims. For the sake of completeness reference is also made to the fact that use of the indefinite article "a" or "an" does not preclude the relevant features from also being present multiple times. Similarly, the term "unit" does not preclude this from being composed of a plurality of components, which can optionally also be spatially distributed. Independent of the grammatical term usage, individuals with male, female or other gender identities are included within the term.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The expression "a number of" means "at least one". The mention of a "unit" or a "device" does not preclude the use of more than one unit or device. The expression "a number of" has to be understood as "at least one".

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

The invention claimed is:

1. A method for generating a plurality of contrast-enhanced mammograms of an examination region, the method comprising:

defining a plurality of at least two different angular positions for a tomosynthesis projection recording;

generating at least two low-energy tomosynthesis projection recordings of the examination region from the at least two different angular positions in a presence of a contrast agent;

generating at least two high-energy tomosynthesis projection recordings of the examination region from the at least two different angular positions in the presence of the contrast agent; and generating at least two contrast-enhanced mammograms by subtracting the respective low-energy tomosynthesis projection recording from the respective high-energy tomosynthesis projection recording for a respective angular position.

2. The method of claim 1, wherein the plurality of at least two different angular positions comprises at least three different angular positions, the at least three different angular positions are divided into first angular positions and second angular positions, wherein the second angular positions comprise at least two different angular positions, the low-energy tomosynthesis projection recordings are generated s sting-from the first angular positions and the second angular positions, the high-energy tomosynthesis projection recordings are generated from the second angular positions, and a recombined tomosynthesis representation is generated based on the low-energy tomosynthesis projection recordings.

3. The method of claim 2, wherein the generating the low-energy tomosynthesis projection recordings at the first angular positions includes, using a first current-time product for actuating an X-ray source for generating the low-energy tomosynthesis projection recordings, and the generating the low-energy synthesis projection recordings at the second angular positions includes using a second current-time product for actuating the X-ray source for generating the low-energy tomosynthesis projection recordings; and the generating the high-energy tomosynthesis projection recordings includes, using the second current-time product for actuating the X-ray source for generating the high-energy tomosynthesis projection recordings.

4. The method of claim 3, wherein a value of the second current-time product is higher than a value of the first current-time product.

5. The method of claim 3, wherein the second angular positions comprise the angular position 0°.

6. The method of claim 5, wherein the first angular positions comprise at least three angular positions.

7. The method of claim 6, wherein the second angular positions are defined as a function of at least one of the angular positions of previous recordings, or a z-position of a suspected lesion.

8. The method of claim 7, further comprising:

generating at least two mid-energy tomosynthesis projection recordings of the examination region from the at least two different angular positions, in a presence of the contrast agent for at least one mid X-ray energy, the mid X-ray energy being between the low energy and the high energy; and generating material-specific mammograms based on the two mid-energy tomosynthesis projection recordings.

9. The method of claim 2, wherein the second angular positions comprise at least the angular positions of −15° and +15°.

10. The method of claim 2, wherein the second angular positions comprise the angular position 0°.

11. The method of claim 2, wherein the first angular positions comprise at least three angular positions.

12. The method of claim 11, wherein the first angular positions comprise between nine and 22 angular positions.

13. The method of claim 2, wherein the second angular positions are defined as a function of at least one of the angular positions of previous recordings, or a z-position of a suspected lesion.

14. The method of claim 2, further comprising:

ascertaining a position of a biopsy needle in at least one of the following image representations, in contrast-enhanced mammograms of the at least two contrast-enhanced mammograms, which are based on the tomosynthesis projection recordings of the second angular positions, in the low-energy tomosynthesis projection recordings of the second angular positions, or in the recombined tomosynthesis representations of the low-energy tomosynthesis projection recordings of at least one of the first angular positions or second angular positions.

15. The method of claim 1, further comprising:

generating at least two mid-energy tomosynthesis projection recordings of the examination region from the at least two different angular positions, in a presence of the contrast agent for at least one mid X-ray energy, the mid X-ray energy being between the low energy and the high energy; and generating material-specific mammograms based on the two mid-energy tomosynthesis projection recordings.

16. The method of claim 1, further comprising:

ascertaining one of the following image representations-based on the generated tomosynthesis projection recordings, a digital recombined low-energy breast tomosynthesis representation, a synthetic low-energy 2D mammogram, a contrast-enhanced recombined tomosynthesis representation, a mammogram processed from a tomosynthesis projection recording for a second angular position, a contrast-enhanced mammogram for a second angular position, the contrast-enhanced mammogram for the second angular position being one of the at least two contrast-enhanced mammograms, or a projection recording of a low-energy tomosynthesis projection recording overlaid with an image representation of a contrast-enhanced mammogram; and supplying the ascertained image representation to a user.

17. A mammography system including a mammography processor, the mammography processor configured to cause the mammography system to:

define a plurality of at least two different angular positions for a contrast-enhanced tomosynthesis projection recording of an examination region, generate at least two low-energy tomosynthesis projection recordings of the examination region, from the at least two different angular positions, in a presence of a contrast agent, generate at least two high-energy tomosynthesis projection recordings of the examination region, from the at least two different angular positions, in the presence of a contrast agent; and generate at least two contrast-enhanced mammograms by subtracting the respective low-energy tomosynthesis projection recording from the respective high-energy tomosynthesis projection recording for a respective angular position.

18. A mammography system, comprising:

an X-ray source configured to emit X-ray radiation;

an X-ray detector unit configured to detect the emitted X-ray radiation; and the mammography processor of claim 17, the mammography processor configured to actuate the X-ray source and evaluate the X-ray radiation detected by the X-ray detector unit.

19. A non-transitory computer program product including program segments, which when executed by a computing unit, cause the computing unit to perform the method of claim 1.

20. A non-transitory computer-readable medium including program segments, which when executed by a computing unit, cause the computing unit to perform the method of claim 1.

\*    \*    \*    \*    \*